(12) United States Patent
Burnam et al.

(10) Patent No.: US 12,427,321 B2
(45) Date of Patent: Sep. 30, 2025

(54) INTELLIGENTLY, CONTINUOUSLY AND PHYSIOLOGICALLY CONTROLLED PACEMAKER AND METHOD OF OPERATION OF THE SAME

(71) Applicant: BaroPace, Inc., Ashland, OR (US)

(72) Inventors: Michael Burnam, Ashland, OR (US); Eli Gang, Los Angeles, CA (US)

(73) Assignee: BaroPace, Inc., Ashland, OR (US)

( * ) Notice: Subject to any disclaimer, the term of this patent is extended or adjusted under 35 U.S.C. 154(b) by 552 days.

(21) Appl. No.: 17/434,681

(22) PCT Filed: Mar. 27, 2020

(86) PCT No.: PCT/US2020/025447
§ 371 (c)(1),
(2) Date: Aug. 27, 2021

(87) PCT Pub. No.: WO2020/210060
PCT Pub. Date: Oct. 15, 2020

(65) Prior Publication Data
US 2022/0040487 A1    Feb. 10, 2022

Related U.S. Application Data

(63) Continuation-in-part of application No. PCT/US2019/059703, filed on Nov. 4, 2019.
(Continued)

(51) Int. Cl.
*A61N 1/00* (2006.01)
*A61N 1/37* (2006.01)
(Continued)

(52) U.S. Cl.
CPC .......... *A61N 1/3702* (2013.01); *G16H 10/60* (2018.01); *G16H 20/40* (2018.01)

(58) Field of Classification Search
None
See application file for complete search history.

(56) References Cited

U.S. PATENT DOCUMENTS

| | | |
|---|---|---|
| 4,791,931 A | 12/1988 | Slate |
| 5,129,394 A | 7/1992 | Mehra |

(Continued)

FOREIGN PATENT DOCUMENTS

| | | |
|---|---|---|
| CA | 2195018 A1 | 2/1996 |
| CN | 203494057 U | 3/2014 |

(Continued)

OTHER PUBLICATIONS

Extended European search report in European Application No. 20786932.2, dated May 24, 2022 (6 pages).
(Continued)

*Primary Examiner* — Sana Sahand
(74) *Attorney, Agent, or Firm* — DLA PIPER LLP (US)

(57) ABSTRACT

A pacemaker control system includes a pacemaker; a plurality of sensors which are internal to the pacemaker, a plurality of sensors which are external to the pacemaker, a circuit for entering patient reports; and a circuit for using artificial intelligence to process outputs from the plurality sensors internal and external to the pacemaker and from the circuit for entering patient reports, which are collectively identified as a labeled dataset, to reiteratsvely learn a function which determines the labeled dataset most likely to provide optimal pacemaker function for the patient. The means for using artificial intelligence comprises a database of archive outputs from the plurality sensors internal and external to the pacemaker and from the means for entering patient reports for the patient used for optimization of rate modulation to intelligently, continuously and physiologically control the pacemaker.

20 Claims, 2 Drawing Sheets

Related U.S. Application Data

(60) Provisional application No. 62/833,052, filed on Apr. 12, 2019.

(51) Int. Cl.
*G16H 10/60* (2018.01)
*G16H 20/40* (2018.01)

(56) References Cited

U.S. PATENT DOCUMENTS

| | | |
|---|---|---|
| 5,304,209 A | 4/1994 | Adams et al. |
| 5,904,708 A | 5/1999 | Goedeke |
| 6,141,590 A | 10/2000 | Renirie et al. |
| 7,460,899 B2 | 12/2008 | Almen |
| 7,660,628 B2 | 2/2010 | Libbus et al. |
| 8,046,070 B2 | 10/2011 | Salo et al. |
| 8,086,315 B2 | 12/2011 | Schwartz et al. |
| 8,112,150 B2 | 2/2012 | Naqvi et al. |
| 8,836,535 B2 | 9/2014 | Zhang et al. |
| 9,005,130 B2 | 4/2015 | Fischell et al. |
| 9,155,479 B2 | 10/2015 | Solem |
| 9,433,792 B2 | 9/2016 | Rosenberg et al. |
| 9,636,513 B2 | 5/2017 | Kuo et al. |
| 9,943,263 B2 | 4/2018 | Lee |
| 9,955,289 B1 | 4/2018 | Liu et al. |
| 10,052,494 B2 | 8/2018 | Sheldon et al. |
| 2006/0064134 A1* | 3/2006 | Mazar ............... A61B 5/0215 128/903 |
| 2007/0260285 A1* | 11/2007 | Libbus ............... A61B 5/0205 607/9 |
| 2007/0299477 A1 | 12/2007 | Kleckner et al. |
| 2010/0312125 A1 | 12/2010 | Zhang |
| 2011/0213435 A1 | 9/2011 | Rom |
| 2014/0350630 A1 | 11/2014 | Rosenberg et al. |
| 2016/0175595 A1 | 6/2016 | Lian et al. |
| 2016/0220824 A1 | 8/2016 | Schwartz et al. |
| 2016/0279432 A1 | 9/2016 | Chappel |
| 2017/0304048 A1 | 10/2017 | Mika et al. |
| 2018/0008830 A1* | 1/2018 | Kaiser ............... A61B 5/1459 |
| 2018/0185652 A1 | 7/2018 | Mika et al. |
| 2018/0279889 A1 | 10/2018 | Lee |
| 2018/0359199 A1 | 12/2018 | Nguyen et al. |
| 2019/0004879 A1 | 1/2019 | Chang et al. |
| 2019/0005257 A1 | 1/2019 | Diekmann et al. |

FOREIGN PATENT DOCUMENTS

| | | |
|---|---|---|
| CN | 207707904 U | 8/2018 |
| KR | 20180024266 A | 3/2018 |
| WO | 2012169692 A1 | 12/2012 |
| WO | 2015094401 A1 | 6/2015 |
| WO | 2017117074 A1 | 7/2017 |
| WO | 2020096982 A1 | 5/2020 |

OTHER PUBLICATIONS

Examination Report in corresponding Indian Application No. 202147050504, dated Apr. 27, 2022 (7 pages).

International Search Report in Application No. PCT/US2019/059703, dated Feb. 25, 2020 (2 pages).

International Search Report in Application No. PCT/US2020/025447, dated Sep. 10, 2020 (4 pages).

B. Noll et al., "Influence of Pacing Mode and Rate on Peripheral Levels of Atrial Natriuretic Peptide (ANP)," pace, Nov. 1989, vol. 12; pp. 1763-1768.

International Search Report and Written Opinion in Application No. PCT/US2022/044784, dated Dec. 24, 2020 (8 pages).

M. Birgersson, G. Hansson and U. Franke, "Data Integration Using Machine Learning," 2016 IEEE 20th International Enterprise Distributed Object Computing Workshop (EDOCW), Vienna, Austria, 2016, pp. 1-10, doi: 10.1109/EDOCW.2016.7584357.

\* cited by examiner

INTELLIGENTLY, CONTINUOUSLY AND PHYSIOLOGICALLY CONTROLLED PACEMAKER AND METHOD OF OPERATION OF THE SAME

RELATED APPLICATIONS

The present application is a non-provisional of U.S. provisional application Ser. No. 62/833,052, filed on Apr. 12, 2019, and continuation in part of PCT Patent Application serial no. PCT/US19/59703, filed on Nov. 4, 2019, which are incorporated herein by reference in their entirety and to which priority is claimed pursuant to 35 USG 119, 120, and 365.

BACKGROUND

Field of the Technology

The Invention relates to methods and apparatus for treating diastolic heart failure and for controlling blood pressure in patients, who have proven to be resistant to drug treatments for blood pressure control or independent of drug resistant hypertension (DRH) and diastolic heart failure (DHF) also known as HFpEF, and only requires a patient to have a dual chamber pacemaker or dual chamber defibrillator, arid sick sinus syndrome in the fields characterized by CPC A61N 1/36564; AS 1 N f 13632: A6 I N f/36535; A61N 1/36117: and A6 $_{1N}$ 1/3657 1.

Description of the Prior Art

The normal response of the heart to exercise is an increase in heart rate, modulated by the body's intrinsic cardiac pacemaker structure, the sinus node, located in the right atrium. Activity based rate modulation of permanent pacemakers, as described below, is a feature found in most current pacemakers, which enables an increase in atrial and/or ventricular pacing in response to increased heart rate demands estimated from body motion and respiratory rate in patients who have lost or have a deficiency in that cardiac compensatory mechanism due to disease of the sinus node, called Sick Sinus Syndrome. The degree of additional pacing is estimated and managed externally to the patient predominantly by assessing the patient's symptoms and exercise performance followed by empiric adjustments and further follow-up. Most current pacemakers employ realtime adjustments of rate modulation based upon available physiologic parameters which do not include blood pressure or peripheral resistance. Biotronik SE & Co. KG of Berlin, Germany, offers a so-called "closed loop system" which causes increased pacing when it senses changes in RV contractility via its surrogate (RV impedance) for neurogenic syncope, but the method of operation Is not related in any sense to cardiac management for hypertension.

Pacemaker rate modulation is accomplished using the data from internal pacemaker sensors that currently provide information on body position, respiratory rate, and motion via an accelerometer (piezoelectric crystal most commonly.) At the first visit post implant, the physician or technician typically has the patient walk and then empirically activates the previously inactive rate modulation software estimating what level of assist In heart rate is good for the individual patient taking into consider age, activity level, medications, etc. The activation of rate modulation includes establishing via the pacemaker programmer such parameters a s maximal heart rate, slope of acceleration, and slope of deceleration. The patient is sent home and told to report any unfavorable response to the programming, such as palpitations (feeling excessive heart beat or arrhythmia,) At a return visit, if the patient reports inadequate exercise ability, the physician or technician can increase the parameters, again an empirical adjustment that is manually input by the practitioner. The selected rate modulation will then remain fixed in the pacemaker until a subsequent practitioner-entered adjustment is made, if any.

What is needed is a method and apparatus which can allow an expanded number of sensed inputs from sensors in the pacemaker, from sensors external to the pacemaker and from patient reports to find the optimal rate modulation for the pacemaker for the specific patient at each specific time.

BRIEF SUMMARY

The Pressure Pace pacemaker algorithm as disclosed in the above incorporated PCI Patent Application, PCT/USI9/59703 is enhanced by including as inputs to the pacemaker algorithm:

a. sensor outputs from sensors which are internal to the pacemaker, commonly referred to as the pacemaker sensor suite;
b. sensor outputs from sensors which are external to the pacemaker without limitation as to the kind of sensor; and
c. patient reports, With a large number of sensed or measured Inputs available for determination of the optimal physiologic status, the patient's subjective sense of well-being, and the rate modulation parameters, the calculus quickly overwhelms the practitioner's analytic capability. Thus, the illustrated embodiment includes artificial intelligence that archives all the sensed or measured inputs, establishes historical tables for the specific patient for optimization of rate modulation and learns how to continuously adjust rate modulation based on a multiplicity of internal, external and patient inputs to obtain an optimal rate modulation of the pacemaker for the specific patient What results is an intelligently, continuously and more physiologically controlled pacemaker.

The illustrated embodiments of the invention include a method for operating a pacemaker in a patient including the steps of monitoring blood pressure while using one or more rate modulation sensor outputs from one or more corresponding sensors internal to the pacemaker to improve the accuracy in dynamic states, including when the patient exercises; and controlling rate modulation in the pacemaker in response to the monitored blood pressure and one or more corresponding sensors internal to the pacemaker to selectively prevent excessive pacing to optimize mean arterial blood pressure by either Inhibiting rate modulation in the pacemaker or by changing rate modulation parameters;

The step of monitoring blood pressure includes monitoring systolic blood pressure, diastolic blood pressure, mean arterial pressure, calculated peripheral resistance, and/or calculated systemic vascular resistance, and where controlling rate modulation in the pacemaker includes controlling right atrial pacing as a treatment for drug resistant hypertension and/or diastolic heart failure (HFpEF).

The step of controlling rate modulation in the pacemaker in response to the monitored blood pressure Includes communicating between the pacemaker and an external control circuit.

The stop of communicating between the pacemaker and an external control circuit includes communicating via a Bluetooth or similar link, temporary wires with adhesive pads, permanent wires, or an optical linkage with a fiber optic cable.

The step of monitoring blood pressure includes monitoring blood pressure with a pneumatic cuff, or devices without pneumatic cuffs such as a wristwatch-type using two photoplethysmogram (PPG) signals as source for the blood pressure estimation, an electro-optical technique, or an intracardiac pressure sensor In one or more heart chambers.

The step of controlling rate modulation in the pacemaker includes controlling rate modulation in using one or more rate modulation sensors worn by the patient and not In the pacemaker itself, including, but not limited to an accelerometer, a body position sensor, a respiratory rate monitor, a cardiac impedance sensor, pulse oximeter, an EGG monitor for heart rate and arrhythmias, intracardiac chamber pressure sensors, such as RA, LA, RV, or LV, or intracardiac chamber volume measurements in ail four chambers measured by either intra-cavatary impedance, capacitance, ultrasound, skin chemical, skin impedance, or pulse oximetry.

The method further includes the step of using artificial intelligence to make decisions regarding an optimal pacing rate taking ail variables into consideration selected from the group including the patient's age, race, sex, prior history of heart disease, prior known let ventricular function, medications, type, mode!, and manufacturer of pacemaker, and all sensor type inputs, whereby artificial intelligence is utilized to process all variables to arrive at the best possible pacing rate at each moment of time at a sensed level and type of exercise for the patient, faking into account any prior attempts by the patient to perform the same activity, to anticipate the needs for that similar exercise session, any recent changes in the patient's health or medication that might impact exercise performance, the ambient oxygen level and altitude, the temperature of the environment.

The illustrated embodiments also include a computer implemented method for optimizing the function of a patient's pacemaker comprising utilizing an implanted pacemaker with rate modulation; and controlling pacemaker rate modulation to enhance exercise ability by using data obtained from a sensor platform external to the pacemaker by using a reported patient's subjective sense of comfort, measured exercise duration, optimal workload, optimal heart rate, optimal oxygen consumption, respiratory rate, perspiration, skin impedance, skin temperature, skin or sweat chemistries such as sodium, potassium, chloride and ammonia, glucose and lactic acid, and blood, plasma, or capillary blood measurements such as, but not limited to, brain natriuretic peptide, lactic acid, and cardiac troponin.

The method further Includes the step of optimizing blood pressure at rest and during exercise by using data obtained from a sensor platform external to the pacemaker by using a reported patient's subjective sense of comfort, measured exercise duration, optimal workload, optimal heart rate, optimal oxygen consumption, respiratory rate, perspiration, and/or lowest possible acid production.

The method further includes the step of archiving in a computer system data from all sensors and patient inputs for all sessions.

The step of controlling pacemaker rate modulation is performed using data processing software controlled by artificial intelligence.

The step of controlling pacemaker rate modulation is performed using data processing software controlled by artificial intelligence data mining of all archived data.

The step of controlling pacemaker rate modulation is performed using machine learning from the archived data.

The step of controlling pacemaker rate modulation is performed using artificial intel!igence to process all available instantaneous and archived data io most probably achieve an ideal functional and physiological status of the patient, The step of controlling pacemaker rate modulation Is performed using encrypted pacemaker programming instructions.

The method further includes the step of communicating encrypted pacemaker programming commands wirelessly transmitted to the pacemaker, The method further includes decrypting programming commands to reprogram the pacemaker.

The method further includes the ability to disable or pause any computer program entered into the pacemaker by artificial Intelligence.

The method further includes allowing supervising physician to directly alter programming of the pacemaker to override parameters relating to any ideal data set previously established.

The method further includes remotely programming the pacemaker.

The method further includes remotely programming the sensors that are components of the wearable sensor platform.

The illustrated embodiments of the invention also include a pacemaker control system comprising: a pacemaker; a plurality of sensors which are internal to the pacemaker; a plurality of sensors which are external to the pacemaker: means or circuit for entering patient reports; and means or circuit for using artificial intelligence to process outputs from the plurality sensors internal and external to the pacemaker and from the means for entering patient reports, which are collectively identified as a labeled dataset, to reiteratively learn a function which determines the labeled dataset most likely to provide optimal patient specific pacing prescription includes a range of atrial pacing rates, AV delay settings in patients with conductions system disease, V-V intervals in patients with "Si-Ventricular" pacing systems, and optimal AV delay in patients with 'conduction system pacing' set ups, i.e., His bundle or LBB pacing designs.

The means for using artificial intelligence includes a database of archive outputs from the plurality sensors internal and external to the pacemaker and from the means for entering patient reports for the patient used for optimization of rate modulation to intelligently, continuously and physiologically control the pacemaker.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USG 112 are to be accorded full statutory equivalents under 35 USC 112. The disclosure can be better visualized by turning now to the following drawings wherein like elements are referenced by like numerals.

Figure 1:
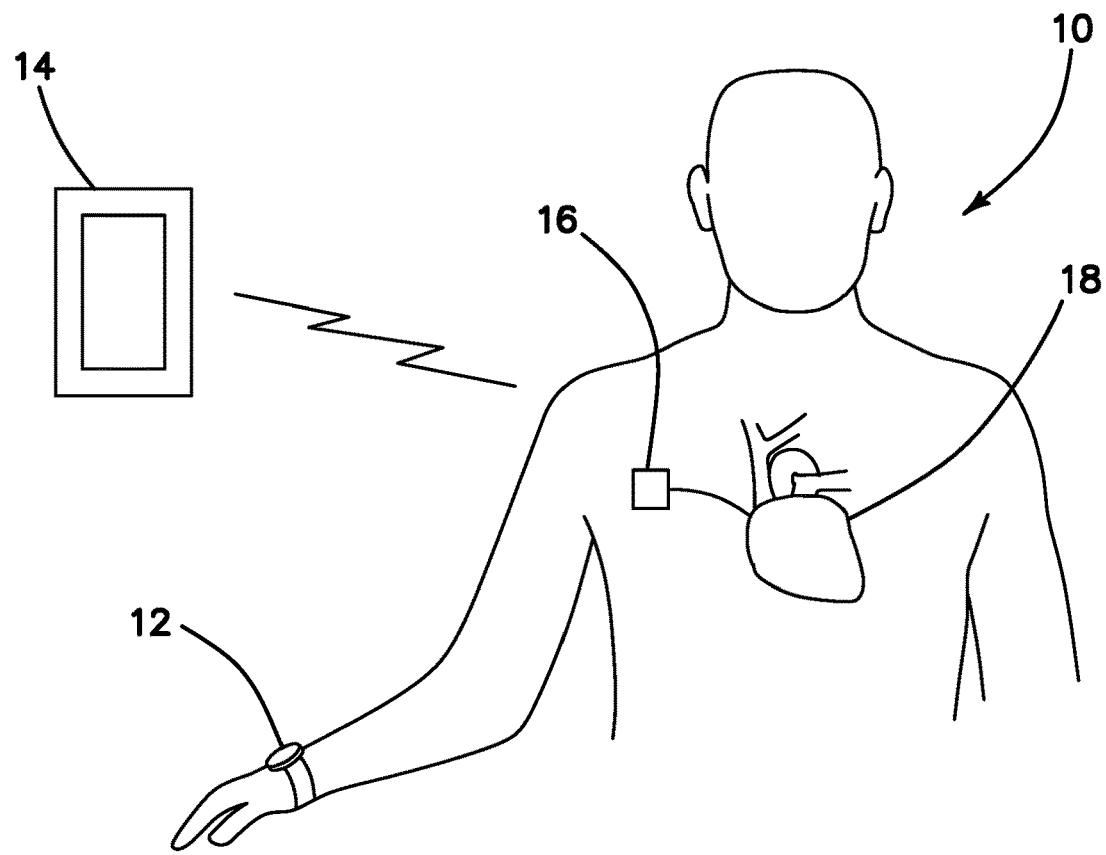
FIG. 1 is a conceptual diagram illustrating the contextual environment of an intelligently, continuously and totally physiologically controlled pacemaker of the illustrated embodiments.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

We have reported and published a relationship between blood pressure and pacemaker-mediated heart rate which is consistent with known physiologic principles, such as v=IR, where v is the change in pressure across the circulation loop (systemic/pulmonary) from its beginning (defined as immediately after exiting the left ventneiemght ventricle) to its end (defined as entering the right atrium/left atrium), I is the flow through the vasculature (when discussing systemic vascular resistance (SVR) this Is equal to cardiac output) and R is resistance to flow.

An algorithm has been developed, commercially labeled and for the purposes of this specification defined as PressurePace is disclosed in the above incorporated PCT Patent Application, PCT/US 19/59703. We have observed clinical performance in patients with aortic valvular stenosis and pacemakers containing conventional rate modulation software during a standard exercise treadmill test. As expected, during exercise the combination of increased respiratory activity and body motion as sensed and processed by the pacemaker's conventional rate modulation software resulted in progressively faster paced heart rates, often to the maximum programmed pacing rate at an early stage of exercise. The most common outcome was the patient requesting to stop exercise due to a combination of fatigue, shortness of breath, and often dizziness. This was often accompanied by a drop in systolic blood pressure that was attributed b aortic valvar stenosis according to accepted physiologic principles.

We have repeated the treadmill test a week or more later in the same patient acting as his own control with the conventional rate modulation software temporarily disabled. The patient's exercise performance usually significantly improved and the blood pressure either didn't fail at all, or fell b a lesser degree without the patient complaining of dizziness. It was therefore reasoned that the conventional rate modulation software which, in the absence of an algorithm like PressurePace, did not take into account the patient's blood pressure, had inappropriately elevated heart rate causing the blood pressure to fall.

The previously described algorithm, PressurePace, improves rate modulation in pacemakers by adding the variables of optimum blood pressure (systolic, diastolic, and mean,) and peripheral resistance. PressurePace calculates optimum right atrial pacing output using the existing rate modulation sensor outputs without modification, This disclosure describes a further embodiment of the PressurePace pacemaker algorithm that integrates additional pacemaker rate modulation sensor outputs typically included in the pacemaker sensor suite for enhanced performance. In addition to utilizing sensor outputs from sensors included in the pacemaker, physiological sensor inputs from sensors external to the pacemaker are included, including blood pressure measurements and all other kinds of external data outputs without limitation. In addition to utilizing interna! and external pacemaker sensor outputs, patient reports are Included as inputs into the pacemaker algorithm. Patient reporting in one embodiment is provided as a function on the blood pressure watch or other similar platform which allows the patient to input as nonlimiting examples; "shortness of breath on a scale ranging from 0=none, to 5=stop exercising; and "heart beating too fast, on a scale of 0=not at all, to 5=intolerable.

Examples of rate modulation sensors used in the enhanced performance embodiment include,: but are not limited to:
 a. Accelerometers (piezoelectric crystals are the most common type.)
 b. Body position sensors
 c. Respiratory Rate Monitors
 d. Infra cardiac chamber pressure measurements, such as right atrial (RA), left atrial (LA), right ventricle (RV), or left ventricle (LVi
 e. Infra cardiac chamber volume measurements in all four chambers, measured by either intra-cavatary impedance, capacitance, or ultrasound In one illustrated embodiment, as diagrammatically shown in FIG. 1, blood pressure is measured by a wristwatch sensor 12 worn by patient 10 and transmitted via blue tooth connectivity to an smartphone 14 containing PressurePace in an app. The patient's body movement is measured by a piezoelectric crystal in the pacemaker 16, which is implanted and communicated to the heart 18, the result is encrypted, and transmitted via Bluetooth connectivity to the smartphone app containing PressurePace. The patient's respiratory rate is also measured by the pacemaker's 16 onboard respiratory rate monitor, the result is encrypted, and transmitted via Bluetooth connectivity to the smartphone app containing PressurePace. PressurePace receives and decrypts the blood pressure, accelerometer, and respiratory rate monitor outputs from pacemaker 18 and wrist sensor 12, PressurePace uses the blood pressure, accelerometer output, and respiratory rate monitor outputs to calculate the patient's optimum pacemaker right atrial pacing rate. The optimal pacemaker right! atrial pacing rate calculated by PressurePace is encrypted and transmitted back to the pacemaker 18 and the pacemaker right atrial pacing rate is increased, decreased, or left unchanged. The entire foregoing process is repeated in three minutes intervals of such other intervals as desired, Besides the PressurePace algorithm which adds blood pressure, the addition of other variables which have a potentially physiologic relationship to the patient's heart rate response, but are not currently used to optimize rate modulation could be included. Examples could include, but are not limited to:
 a. Ambient temperature
 b. Oxygen uptake (a measure of work load)
 c. Ambient oxygen percentage (varies with altitude)
 d. Blood pH (acid content)
 e. Expired $CO_2$ levels
 f. The time of day
 g. Heart rate at beginning of exercise
 h. Skin chemistries or skin electrolytes (sodium and potassium)
 i. Water content (index of perspiration)
 j. Carbohydrate content, such as glucose and glucose breakdown products
 k. Wetness or sweat measures such as water content, salt, etc.
 l. Galvanic skin resistance
 m. Breath content analysis n. Saliva analysis
o. ECG patterns
p. internal organ indicators
q. Patient reporting Sensors exist now for ail these variables. Some are already integrated into watch-like platforms.

With the number and variety of kinds of sensed or reported inputs increased to a large dataset, optimal adjustment of the rate modulation by the practitioner becomes impractical and exceeds the practitioner's analytical abilities. Artificial intelligence (AI) is used to integrate such parameters in an advanced PressurePace algorithm. The advanced or modified PressurePace algorithm is defined as PressurePaceAS and optimizes rate modulation by either increasing, decreasing, or leaving as is the right atrial pacing rate along with standard rate modulation pacemaker derived "decisions", but with an altered slope, duration, maximal pacing rate, measurement interval, deceleration rate, as a noninclusive list of possible pacing parameter adjustments.

Figure 2:
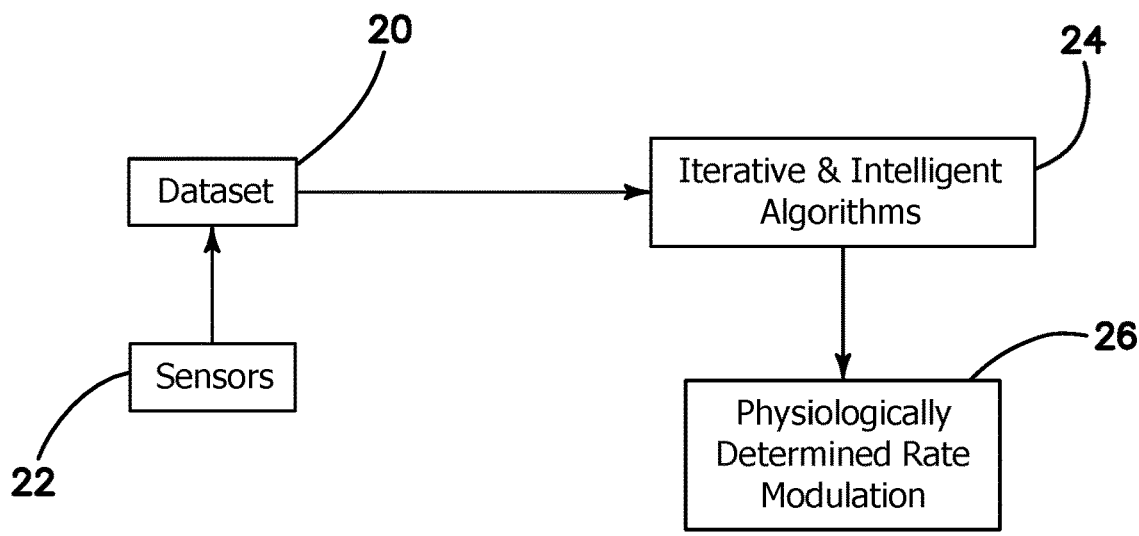
FIG. 2 is a block diagram illustrating the principal components of a PressuePace AI system.

As symbolically depicted in FIG. 2, AI works by combining large amounts of data in an archived dataset 20 collecting and archiving data from a sensor suite 22 with fast, iterative processing and intelligent algorithms 24, allowing the software to learn automatically from patterns or features in the data. Machine learning feeds a computer database and uses statistical techniques to help it "learn" how to get progressively better at a task, without having been specifically programmed for that task, eliminating the need for millions of lines of written code. Machine learning consists of both supervised learning (using labeled data sets) and unsupervised learning (using unlabeled data sets). PressurePace AI preferably uses supervised learning, but is not limited thereto.

Machine learning (ML), a fundamental concept of AI research since the field's inception, is the study of computer algorithms that improve automatically through experience. Unsupervised learning is the ability to find patterns in a stream of input, without requiring a human to label the inputs first Supervised learning includes both classification and numerical regression, which requires a human to label the input data first. Classification is used to determine what category something belongs in, and occurs after a program sees a number of examples of things from several categories. Regression is the attempt to produce a function that describes the relationship between inputs and outputs and predicts how the outputs should change as the Inputs change. Both classifiers and regression learners can be viewed as "function approximators" 26 trying to learn an unknown (possibly implicit) function; for example, a cardiac classifier can be viewed as learning a function that maps from the a database of multiple physiologic inputs to one of two categories, "improved cardiac function" or "not improved cardiac function". Computational teaming theory can assess learners by computational complexity, by sample complexity (how much data is required), or by other notions of optimization, in reinforcement learning an agent is "rewarded" for good responses and "punished" for bad ones. The agent uses this sequence of rewards and punishments to form a strategy for operating in its problem space.

AI analyzes its environment, namely the available sensor outputs, and identifies the data set that maximizes the chance to achieve the ideal data set using statistics. The ideal data set is or may be initially defined by the supervising physician. Noninclusive examples of the variables in the ideal data set include those listed above, but are not limited to exercise duration, peak heart rate, peak respiratory rate, zero percent skin wetness, and patient reports of how they feel that contain no adverse ratings.

Figure 3:
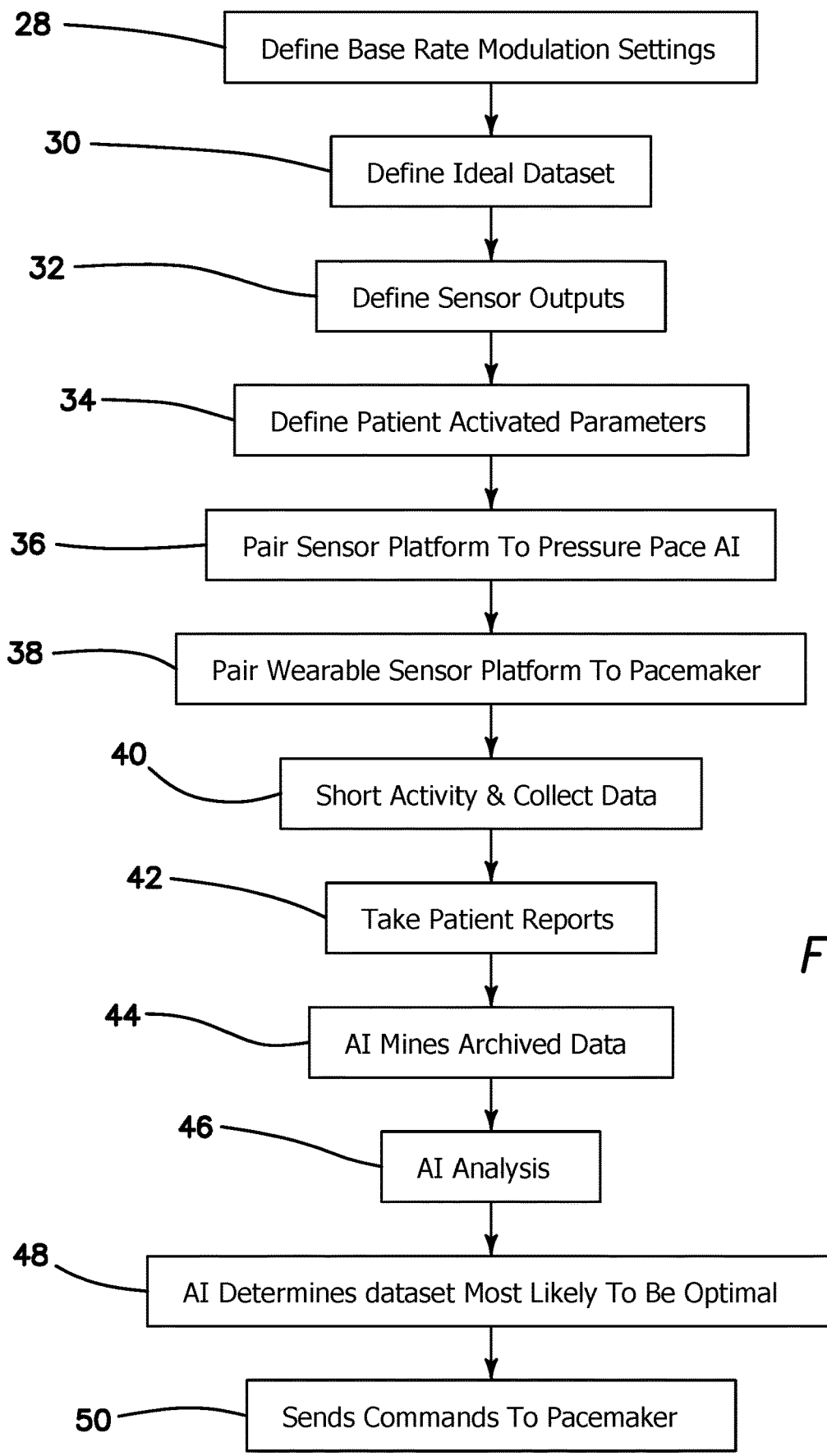
FIG. 3 is a flow diagram of an embodiment of a method of operation of the PressurePace AI system.

A version of PressurePace AI employing A software resident in an app is illustrated in FIG. 3 by the following. For the sake of this example, assume data has been archived from prior exercise sessions. The Ai could be resident in an app integrated into the wearable sensor platform, inside a separate device such as a smartphone, or inside the pacemaker itself.

a. Define baseline rate modulation settings if activated at step 28,
b. The attending physician defines the ideal data set in the first session at step 30.
c. Define available sensor outputs available, such as systolic blood pressure, heart rate, respiratory rate, pulse oximetry, ambient temperature, attitude, sweat chemistry at step 32.
d. Define patient activated parameters at step 34. The patient's wearable sensor platform or smartphone containing the various sensors including blood pressure, and PressurePace AI, also has patient activated buttons, such as:
  i. Examples of adverse events reported by the patient: Heart beat too fast. Feet skips. Shortness of breath, Feel worse than before (Scale of 1-5 with 5 being worst rating),
  ii. Positive events: Feels good. Feels better than before {Scale of 1-5 with 5 b being the highest rating.)
e. Pair wearable sensor platform with PressurePace AI app at step 36.
f. Pair wearable containing app with pacemaker at step 38.
g. Begin activity and collect data at step 40.
h. Patient reports how he feels at frequent intervals at step 42.
i. AI data mines all parameters from prior sessions at step 44.
j. AI performs multivariate analysis at 1 second intervals at step 46.
k. AI compares current parameter set to the ideal data set and prior session's parameter sets. AI uses a standard statistical package to determine which data set is most likely to produce the optimum data set, namely the closest parameter set to the ideal data set with the least reported patient adverse responses at step 48.
l. PressurePace AI sends commands the pacemaker to adjust those parameters that require adjustment to better approximate the parameter set most likely to achieve the ideal data set as step 50
m. The entire process is repeated by returning to the data collection of step 40.

Many alterations and modifications may be made by those having ordinary skill in the art without departing from the spirit and scope of the embodiments. Therefore, it must be understood that the illustrated embodiment has been set forth only for the purposes of example and that it should not be taken a s limiting the embodiments a s defined by the following embodiments and its various embodiments, Therefore, it must be understood that the i!Sustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if a n element can be understood In the context of this specification as including more than one meaning, then its use in a claim must he understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed b a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conoeptionalty equivalent, what can be obviously substituted and also what essentially incorporates the essential idea of the embodiments.

We claim:

1. A system for cardiac pacing comprising:
a heart pacing device;
at least one memory storing instructions; and
at least one processor executing the instructions to perform operations, the operations comprising:
receiving an ideal dataset comprising a plurality of ideal patient parameters for a patient, at a machine learning model;
receiving a plurality of archived datasets at the machine learning model, each archived dataset comprising historical physiological variables, corresponding historical patient parameters, or corresponding historical rate modulation parameters;
receiving, at the machine learning model, current physiological variables from one or more sensors;
identifying, by the machine learning model, an optimal archived dataset, from the plurality of archived datasets, based on the optimal archived dataset having a first threshold match between the current physiological variables and optimal historical physiological variables of the optimal archived dataset and further based on the optimal archived dataset having a second threshold match between the ideal patient parameters and optimal historical patient parameters of the optimal archived dataset;
outputting, by the machine learning model, to the heart pacing device, new rate modulation parameters based on optimal historical rate modulation parameters of the identified optimal archived dataset, wherein the new rate modulation parameters increase or decrease a heart rate of the patient; and
stimulating, by the heart pacing device, the heart of the patient at the new rate modulation parameters.

2. The system of claim 1, wherein the ideal parameters comprise at least one of an optimal blood pressure, an optimal exercise duration, an optimal heart rate, an optimal respiratory rate, an optimal skin wetness, an optima perspiration, an optimal skin impedance, an optimal temperature, an optimal skin or sweat chemistry, or a threshold adverse rating.

3. The system of claim 1, wherein the plurality of archived datasets are received from the at least one memory.

4. The system of claim 1, wherein the at least one of the processor or the machine learning model is part of a wearable device, a smartphone, or a cardiac pacing device.

5. The system of claim 1, wherein the new rate modulation parameters comprise one or more of a pacing rate, a slope of acceleration of pacing, a pacing duration, or a slope of deceleration of pacing.

6. The system of claim 1, wherein the one or more sensors are one of wearable sensors, cardiac pacing device sensors, or lead sensors.

7. The system of claim 6, further comprising a wearable sensor platform comprising the wearable sensors, the wearable sensors including one or more of a rate modulation sensor, an accelerometer, a body position sensor, a respiratory rate sensor, a pulse oximeter, an intra cardiac chamber pressure sensor, an intra cardiac volume pressure sensor, an ambient temperature sensor, an oxygen sensor, a blood pH sensor, a carbon dioxide sensor, a time output sensor, a heart rate sensor, a skin chemistry sensor, a skin electrolyte sensor, a water sensor, a carbohydrate sensor, a sweat sensor, a galvanic skin resistance sensor, a breath sensor, a saliva sensor, an electrocardiogram (ECG) sensor, an organ sensor, or a patient input device.

8. The system of claim 6, wherein the wearable sensors are housed in a wrist watch.

9. The system of claim 6, further comprising a cardiac pacing device.

10. The system of claim 9, wherein the cardiac pacing device sensors are housed in the cardiac pacing device and include one or more of an accelerometer, a body position sensor, a respiratory rate sensor, a intra cardiac chamber pressure sensor, or an intra cardiac chamber volume sensor.

11. The system of claim 1, wherein each archived dataset further comprises additional historical variables corresponding to respective historical physiological variables, the additional historical variables including one or more of a historical patient age, a historical patent race, a historical patient sex, a historical patient medical history, a historical patient's prior known chamber function, historical patient medications, or historical cardiac pacing device attributes.

12. The system of claim 11, wherein the optimal archived dataset is identified further based on a third threshold match between the additional historical variables of the optimal archived dataset and respective additional current variables for the patient or cardiac device.

13. A system for cardiac pacing comprising:
a heart pacing device;
at least one memory storing instructions; and
at least one processor executing the instructions to perform operations, the operations comprising:
receiving an ideal patient blood pressure, at a machine learning model;
receiving a plurality of archived datasets at the machine learning model, each archived dataset comprising historical physiological variables, corresponding historical blood pressure values, or corresponding historical rate modulation parameters;
receiving, at the machine learning model, current physiological variables from a wearable sensor;
identifying, by the machine learning model, an optimal archived dataset, from the plurality of archived datasets, based on the optimal archived dataset having a first threshold match between the current physiological variables and optimal historical physiological variables of the optimal archived dataset and further based on the optimal archived dataset having a second threshold match between the ideal blood pressure and optimal historical blood pressure of the optimal archived dataset;
outputting, by the machine learning model, to the heart pacing device, new rate modulation parameters based on optimal historical rate modulation parameters of the identified optimal archived dataset, wherein the new rate modulation parameters increase or decrease a heart rate of the patient; and
stimulating, by the heart pacing device, the heart of the patient at the new rate modulation parameters.

14. The system of claim 13, wherein the ideal patient blood pressure is provided from a wearable blood pressure sensor.

15. The system of claim 13, wherein the ideal patient blood pressure is provided from a cardiac pacing device blood pressure sensor or a lead blood pressure sensor.

16. The system of claim 13, wherein the plurality of archived datasets are stored in the at least one memory.

17. The system of claim 13, wherein the at least one of the processor or the machine learning model is part of a wearable device, a smartphone, or a cardiac pacing device.

18. A method for cardiac pacing, the method comprising:
receiving an ideal dataset comprising a plurality of ideal patient parameters for a patient, at a machine learning model;
receiving a plurality of archived datasets at the machine learning model, each archived dataset comprising historical physiological variables, corresponding historical patient parameters, or corresponding historical rate modulation parameters;
receiving, at the machine learning model, current physiological variables from one or more sensors;
identifying, by the machine learning model, an optimal archived dataset, from the plurality of archived datasets, based on the optimal archived dataset having a first threshold match between the current physiological variables and optimal historical physiological variables of the optimal archived dataset and further based on the optimal archived dataset having a second threshold match between the ideal patient parameters and optimal historical patient parameters of the optimal archived dataset;
outputting, by the machine learning model, to a heart pacing device, new rate modulation parameters based on optimal historical rate modulation parameters of the identified optimal archived dataset, wherein the new rate modulation parameters increase or decrease a heart rate of the patient and
stimulating, by the heart pacing device, the heart of the patient at the new rate modulation parameters.

19. The method of claim 18, wherein the new rate modulation parameters comprise one or more of a pacing rate, a slope of acceleration of pacing, a pacing duration, or a slope of deceleration of pacing.

20. The method of claim 18, wherein the one or more sensors are one of wearable sensors, cardiac pacing device sensors, or lead sensors.

* * * * *